United States Patent [19]

Sanderson et al.

[11] Patent Number: 4,922,034

[45] Date of Patent: May 1, 1990

[54] CATALYZED CONVERSION OF TERTIARY BUTYL HYDROPEROXIDE TO TERTIARY BUTYL ALCOHOL

[75] Inventors: John R. Sanderson, Leander; Edward T. Marquis; Mark A. Mueller, both of Austin, all of Tex.

[73] Assignee: Texaco Inc., White Plains, N.Y.

[21] Appl. No.: 94,172

[22] Filed: Sep. 8, 1987

[51] Int. Cl.$^5$ .................. C07C 31/12; C07C 29/132; C07C 29/88; C07C 27/04

[52] U.S. Cl. .................. 568/909.8; 502/167; 568/910; 568/914; 568/922; 568/571

[58] Field of Search ............... 568/571, 840 A, 910, 568/914, 922, 909.8; 502/167

[56] References Cited

U.S. PATENT DOCUMENTS

| | | | |
|---|---|---|---|
| 3,360,585 | 12/1967 | Winnick | 568/840 |
| 3,505,360 | 4/1970 | Allison et al. | 568/840 |
| 4,508,923 | 4/1985 | Taylor et al. | 568/840 |
| 4,547,598 | 10/1985 | Sanderson et al. | 568/840 |
| 4,551,553 | 11/1985 | Taylor et al. | 568/840 |

FOREIGN PATENT DOCUMENTS 1212824 11/1970 United Kingdom ............. 568/909.8

*Primary Examiner*—Vivian Garner
*Attorney, Agent, or Firm*—Jack H. Park; Kenneth R. Priem; Carl G. Ries

[57] ABSTRACT

Tertiary butyl alcohol is prepared by the catalytic decomposition of tertiary butyl hydroperoxide, preferably in solution in tertiary butyl alcohol, in the presence of a metal porphine catalyst, optionally promoted with a $C_1$ to $C_{18}$ alkyl thiol and an amine, such as an iron (III) or manganese (III) porphine and, optionally, a thiol such as dodecane thiol and an amine, such as a heterocyclic amine (e.g., pyridine, quinoline, isoquinoline, imidazole or a 1-alkyl or 2-alkyl imidazole).

17 Claims, No Drawings

CATALYZED CONVERSION OF TERTIARY BUTYL HYDROPEROXIDE TO TERTIARY BUTYL ALCOHOL

BACKGROUND OF THE INVENTION

1. Field of the Invention

This invention relates to the catalytic decomposition of tertiary butyl hydroperoxide. More particularly, this invention relates to a method for the preparation of tertiary butyl alcohol by the catalytic decomposition of tertiary butyl hydroperoxide. Still more particularly, this invention relates to a method wherein the substantially selective decomposition of tertiary butyl hydroperoxide to tertiary butyl alcohol is accomplished in the presence of catalyst composed of a metal porphine such as an iron (III) or manganese (III) porphine and, optionally, a mercaptan and/or an amine.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

The metal phthalocyanines are known compounds, described for example in the ACS Monograph Series by F. H. Moser and A. L. Thomas entitled "Phthalocyanine Compounds" (Rhinehold Publishing Corp.).

Williams et al. U.S. Pat. No. 3,816,548 is directed to a liquid phase oxidation process for oxidizing an isoparaffin hydrocarbon such as isobutane to an alcohol such as tertiary butyl alcohol in the presence of certain metal phthalocyanine catalysts.

Klein in U.S. Pat. No. 3,472,876, discloses the use of cobalt diimine chelates to catalyze the reaction of oxygen with an olefin to form an olefin epoxide.

Quin U.S. Pat. No. 2,854,487 discloses a process wherein isopropyl benzene hydroperoxides are catalytically decomposed to form carbinols in the presence of hydrogen and a catalyst composed of palladium supported on activated alumina.

Grane U.S. Pat. No. 3,474,151 discloses that tertiary butyl alcohol starts to dehydrate at 450° C. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 75° for about 1 to 10 minutes.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°–350° F. at a pressure lower than the pressure in the oxidation zone. The tertiary butyl alcohol can be further subjected to a cleanup treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

When isobutane is reacted with molecular oxygen, the principal products of the reaction are tertiary butyl alcohol and tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

A listing of the components present in a representative reaction product from the reaction of isobutane and oxygen and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| Tertiary butyl hydroperoxide | 118.9 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl hydroperoxide but tends to distill overhead, which suggests that it forms a minimum boiling azeotrope with another component or components.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

In accordance with the present invention, isobutane is reacted with oxygen in an oxidation zone to provide an oxidation product comprising a solution of tertiary butyl hydroperoxide in unreacted isobutane. A catalyst may be present to catalyze the reaction of the oxygen with the isobutane if desired.

A suitable feedstock is used, such as one prepared by the oxidation of isobutane with molecular oxygen to provide an oxidation reaction product containing a solution of tertiary butyl hydroperoxide in unreacted isobutane. The feedstock may comprise tertiary butyl hydroperoxide dissolved in tertiary butyl alcohol which is recovered from the oxidation reaction product. The feedstock is charged to a catalytic decomposition zone wherein the tertiary butyl hydroperoxide is decomposed in the presence of a catalyst of the present invention to provide a decomposition reaction product characterized by a comparatively high conversion rate and a comparatively high selectivity of tertiary butyl hydroperoxide to tertiary butyl alcohol.

The tertiary butyl alcohol will not be the only decomposition product that is formed. A minor amount of ditertiary butyl peroxide will also be formed together with other oxygen-containing materials such as those listed above.

The tertiary butyl alcohol that is recovered from the decomposition reaction mixture will be contaminated with ditertiary butyl peroxide and other oxygenated impurities.

The ditertiary butyl peroxide can be recovered, if desired, by a process such as the process disclosed in copending Sanderson et al. U.S. patent application Ser. No. 06/945,628, filed Dec. 23, 1986, and entitled "Recovery of Purified Ditertiary Butyl Peroxide" or the process disclosed in copending application Ser. No. 06/945,629, filed Dec. 23, 1986 by Sanderson et al., and entitled "Ditertiary Butyl Peroxide Recovery", now U.S. Pat. No. 4,810,809.

If desired, the ditertiary butyl peroxide and other contaminants may be removed from the tertiary butyl alcohol product by a catalytic purification process such as, for example, the purification process disclosed in copending Sanderson et al. U.S. patent application Ser. No. 06/836,798, filed Mar. 6, 1986, now abandoned, and entitled "Removal of Peroxide Contaminants from Tertiary Butyl Alcohol Using a Nickel Catalyst", or by a purification process disclosed in copending Sanderson et al. U.S. patent application Ser. No. 06/926,159, filed Nov. 3, 1986, now U.S. Pat. No. 4,742,179, issued May 3, 1988, and entitled "Catalytic Removal of Peroxide Contaminants from Tertiary Butyl Alcohol" or by the process disclosed in copending Sanderson et al. application Ser. No. 06/932,822, filed Nov. 20, 1986, now U.S. Pat. No. 4,705,903, issued Nov. 10, 1987, and entitled "Catalytic Decomposition of Impurities in Tertiary Butyl Alcohol" or, as yet another example, by the process disclosed in copending Sanderson et al. U.S. patent application Ser. No. 07/004,508, filed Jan. 30, 1987, now U.S. Pat. No. 4,873,380, and entitled "Catalyst for Removing Peroxide Contaminants from Tertiary Butyl Alcohol".

DESCRIPTION OF THE PROCESS OF THE PRESENT INVENTION

The starting materials for the process of the present invention are tertiary butyl hydroperoxide and a solvent, a metal porphine, such as an iron (III) or manganese (III) porphine catalyst. Conversion and/or selectivity are enhanced by using an appropriate mercaptan and/or an amine.

The solvent to be used in practicing the process of the present invention may be any suitable organic solvent in which tertiary butyl hydroperoxide is soluble at least to an extent sufficient to provide a solution containing from about 5 to about 50 wt. % of tertiary butyl hydroperoxide. A preferred solvent is isobutane and a still more preferred solvent is tertiary butyl alcohol or a mixture thereof with isobutane. In accordance with the most preferred embodiment of the present invention, the charge material for the process will comprise about a 5 to about a 30 wt. % solution of tertiary butyl hydroperoxide and tertiary butyl alcohol.

The metal porphine catalysts used in this invention are suitably a porphine of a heavy metal such as, for example, iron (III) meso-tetraphenyl porphine chloride [Fe(III)TPPCl]or manganese (III) meso-tetraphenyl porphine acetate [Mn(III)TPPOAc].

The porphine ring consists essentially of four pyrrole rings

united by methylene groups. When a phenyl group replaces a hydrogen in the methylene group, tetraphenyl porphine (TPP) is the compound.

Tetraphenyl porphine (TPP) may be formed by reaction of benzaldehyde with pyrrole by methods known in the art. The two hydrogens in the center may be replaced by metals such as iron or manganese ions.

Aldrich Catalog (1986-1987), p. 1253, gives a partial listing of the available metal porphines. The metal tetraphenyl porphines are preferred over unsubstituted porphines since they are more readily available and more stable, including compounds such as 5,10,15,20-tetraphenyl-21H,23H-porphine; 5,10,15,20-tetraphenyl-21H,23H-porphine copper; 5,10,15,20-tetraphenyl-21H,23H-porphine iron (III) chloride; 5,10,15,20-tetraphenyl-21H,23H-porphine magnesium; 5,10,15,20-tetraphenyl-21H,23H-porphine manganese (III) chloride; 5,10,15,20-tetraphenyl-21H,23H-porphine nickel (II); 5,10,15,20-tetraphenyl-21H,23H-porphine palladium (II); 5,10,15,20-tetraphenyl-21H,23H-porphine ruthenium (II) carbonyl; 5,10,15,20-tetraphenyl-21H,23H-porphine vanadium (IV) oxide; 5,10,15,20-tetraphenyl-21H,23H-porphine zinc.

The yield and selectivity are improved if the catalyst composition also contains an appropriate mercaptan and/or an appropriate amine.

By way of example, mercaptans that may be used include compounds such as $C_1$ to $C_{18}$ alkyl thiols such as dodecane thiol, butane thiol, hexane thiol, decane thiol, octadecane thiol, etc.

Examples of appropriate amines that may be used include compounds such as pyridine, isoquinoline, imidazole, 1-alkyl or 2-alkyl imidazoles wherein the alkyl group contains 1 to 4 carbon atoms, such as 1-methyl imidazole, 2-methyl imidazole, quinoline, etc.

A catalytically effective amount of the metal porphine (e.g., iron (III) and/or manganese (III) porphine) should be used such as, for example, from about 0.001 to about 5 wt. %, based on the weight of the tertiary butyl hydroperoxide charge and, more preferably, about 0.01 to about 2 wt. %. In accordance with customary practice, from about 0.2 to about 5 parts by weight of mercaptan per part of porphine catalyst may be used, as may from about 0.2 to about 5 parts by weight of amine per part of porphine catalyst.

The process of the present invention may be conducted batchwise in kettles or by continuously passing the reactants through a reactor.

The catalytic decomposition of the tertiary butyl hydroperoxide is preferably conducted at a temperature within the range of about 20° to about 125° C. and, more preferably, at a temperature within the range of about 30° to about 60° C. The reaction is preferably conducted at autogeneous genous pressure although superatmospheric pressures up to about 1000 psig. may be used, if desired.

Flow rates of the charge solution to the reaction zone should be adjusted in order to provide an appropriate contact time within the reactor. In a batch process, the holding time may suitably be from about 0.5 to about 10 hours.

In accordance with the most preferred embodiment of the present invention, isobutane is reacted with oxygen in an oxidation zone under oxidation reaction conditions including a temperature of about 135° to about 155° C., a pressure of about 300 to about 800 psig., and a holding time of about 0.5 to about 5 hours to provide an initial oxidation reaction product comprising unreacted isobutane, tertiary butyl hydroperoxide, and some tertiary butyl alcohol. The oxidation reaction product is fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt. % of tertiary butyl hydroperoxide. If the tertiary butyl hydroperoxide concentration is excessive, additional tertiary butyl alcohol may be added.

The solvent solution of tertiary butyl hydroperoxide in organic solvents (e.g., tertiary butyl alcohol solvent solution of tertiary butyl hydroperoxide) is then charged to a catalytic hydroperoxide decomposition zone where it is brought into contact with an iron III and/or manganese III porphine catalyst to substantially selectively convert the tertiary butyl hydroperoxide to tertiary butyl alcohol with high yields and selectivities.

The reaction product from the tertiary butyl hydroperoxide decomposition step may then be fractionated in any suitable manner, such as, for example, in the manner shown in the process disclosed in above identified copending U.S. patent application Ser. No. 06/945,628 filed Dec. 23, 1986. In accordance with a process recovery sequence of this nature, both the tertiary butyl alcohol and the ditertiary butyl peroxide will be recovered in purified form as products of the reaction.

Alternately, a crude tertiary butyl alcohol product stream contaminated with ditertiary butyl peroxide and other contaminants may be obtained which will then be further treated either thermally, in accordance with the process of the Grane et al. U.S. patents, or catalytically by one of the processes disclosed in the copending Sanderson et al. patent applications to convert the ditertiary butyl peroxide to tertiary butyl alcohol and to otherwise significantly reduce the level of contamination of the other oxygencontaining impurities.

SPECIFIC EXAMPLES

The invention will be further illustrated by the following specific examples which are given by way of illustration and not as limitations on the scope of this invention.

PROCEDURE-1

Tube Experiments

A 150-ml Fisher-Porter pressure tube equipped with pressure gauge, rupture disk, and shut-off valve was charged with 15.0 g of a 20% TBHP solution in TBA, and catalyst(s). The tube was suspended in a constant temperature bath (+ or −0.2° C.) for the desired period of time at the required temperature. The tube was shaken from time to time during the run. At the end of the run, the tube was placed in cold water (15°–20° C.) for 15 minutes. The pressure was then slowly released. The contents were analyzed by GC. The results are shown in the attached Table I.

Procedure-2

A 200 ml round-bottomed flask equipped with magnetic stirrer, water bath, water cooled condenser and thermometer was charged with 20.0 g 20% solution TBHP in TBA. The reaction mixture was vigorously stirred and catalyst(s) added all at once. 1.0 (one) μl aliquots were withdrawn at designated times and analyzed at once by GC. The results are shown in the attached table.

TABLE I

Decomposition of 20% TBHP (in TBA) in the Presence of Various Catalysts

| N.B. Number | Catalyst(s)[a] | Time (Hr) | Temp (°C.) | Wt. % | | | | |
|---|---|---|---|---|---|---|---|---|
| | | | | TBHP | TBA | Acetone | MeOH | DTBP |
| 6224-77 | Ru(AcAc)$_3$ [.005 g] | 1.0 | 60.0 | 0.024 | 96.13 | 1.48 | 0.12 | 1.24 |
| 6225-08 | Mn(III)TPPOAc[.01 g] | 2.0 | 60.0 | 0.048 | 96.36 | 1.38 | 0.08 | 1.30 |
| 6225-10 | Fe(III)TPPCl[.01 g] | 2.0 | 60.0 | 0.012 | 96.12 | 1.73 | 0.14 | 0.96 |
| 6225-34 | Mn(III)TPPOAc[.01 g] | 1.0 | 60.0 | 0.039 | 96.35 | 1.39 | 0.089 | 1.29 |
| 6225-38 | Mn(III)TPPOAc[.01 g] | 2.0 | 40.0 | 2.56 | 93.89 | 0.53 | 0.023 | 2.32 |
| 6225-39 | Mn(III)TPPOAc[.01 g] Py [.05 g] | 2.0 | 40.0 | 0.057 | 95.76 | 0.89 | 0.03 | 2.31 |
| 6225-40 | Mn(III)TPPOAc[.01 g] Py [.05 g] | 2.0 | 40.0 | ~0 | 96.03 | 0.88 | <0.1 | 2.29 |
| 6225-42 | Mn(III)TPPOAc[.01 g] QN [.02 g] | 1.0 | 40.0 | 0.073 | 96.29 | 0.83 | <0.1 | 2.26 |

TABLE I-continued

Decomposition of 20% TBHP (in TBA) in the Presence of Various Catalysts

| N.B. Number | Catalyst(s)[a] | Time (Hr) | Temp (°C.) | TBHP | TBA | Ace-tone | MeOH | DTBP |
|---|---|---|---|---|---|---|---|---|
| 6225-44 | Mn(III)TPPOAc[.01 g] IQN [.01 g] | 2.0 | 40.0 | ~0 | 96.33 | 0.86 | <0.1 | 2.27 |
| 6225-47 | Fe(III)TPPCl[.01 g] Py [.017 g] | 2.0 | 40.0 | 0.41 | 95.71 | 0.77 | <0.1 | 2.58 |
| 6225-27[b] | Ru(AcAc)$_3$ [.005 g] Cr(AcAc)$_3$ [.01 g] | 2.0 | 60.0 | 0.051 | 96.37 | 1.41 | 0.097 | 1.13 |
| — | Starting Material | | | 20.20 | 79.28 | 0.007 | 0 | 0.06 |

[a]AcAc = Acetylacetonate
TPP = Tetraphenylporphine
OAc = Acetate
Py = Pyridine
QN = Quinoline
IQN = Isoquinoline
[b]U.S. Pat. No. 4,551,553 (ARCO)

With reference to Table I, it will be noticed that the use of amines resulted in an enhanced rate of decomposition of the tertiary butyl hydroperoxide as shown by the increased conversion for the given reaction time and an enhanced selectivity of the tertiary butyl hydroperoxide to tertiary butyl alcohol.

At high temperatures (60° C.), it will be noted that <0.04% TBHP remains after 1-2 hours reaction with both Fe and Mn tetraphenyl porphine. Note that the low value by-product acetone >1% under these conditions [see exp. 6225-08, -10, -34]. Ru(AcAc)$_3$ [6224-77]is shown for comparison. At lower temperatures (40° C.) [6225-38], there is substantial TBHP remaining after 2 hours. In the presence of pyridine under the same conditions, there is only a small amount of TBHP remaining [6225-39, -40]. Furthermore, the low value by-product acetone has been reduced to <1%. Quinoline and isoquinoline show the same effect when used in combination with the metal phthalocyanines of this invention. [See 6225-42, -44.]For comparison, an example was run using the catalyst of U.S. Pat. No. 4,551,553 [see 6225-27]. Note that the low value by-product acetone >1% with the catalyst of this system.

TABLE II

Decomposition of TBHP in the Presence of Various Catalysts

| Notebook Number | Time (Hrs) | Temp (°C.) | Catalysts[a] | Reactor[b] | TBHP | TBA | Ace-tone | Meth-anol | DTBP |
|---|---|---|---|---|---|---|---|---|---|
| 6225-59 | .25 | 25.0 | MN(III)TPPOAc (.01 g) IM (.01 g) | F | 15.37 | 83.21 | 0.095 | <0.1 | 0.91 |
| 0059-02 | .75 | 25.0 | MN(III)TPPOAc (.01 g) IM (.01 g) | F | 9.16 | 88.24 | 0.21 | <0.1 | 1.95 |
| 0059-03 | 1.25 | 25.0 | MN(III)TPPOAc (.01 g) IM (.01 g) | F | 7.88 | 89.46 | 0.24 | <0.1 | 2.13 |
| 0059-04 | 1.50 | 25.0 | MN(III)TPPOAc (.01 g) IM (.01 g) | F | 7.36 | 89.80 | 0.22 | <0.1 | 2.18 |
| 0059-05 | 2.50 | 25.0 | MN(III)TPPOAc (.01 g) IM (.01 g) | F | 6.77 | 90.26 | 0.27 | <0.1 | 2.26 |
| 0059-06 | 3.75 | 25.0 | MN(III)TPPOAc (.01 g) IM (.01 g) | F | 6.43 | 90.47 | 0.29 | <0.1 | 2.34 |
| 6225-61 | .15 | 25.0 | MN(III)TPPOAc (.02 g) IM (.02 g) | F | 8.18 | 89.12 | 0.24 | <0.1 | 1.99 |
| 0061-02 | .57 | 25.0 | MN(III)TPPOAc (.02 g) IM (.02 g) | F | 1.73 | 94.41 | 0.45 | <0.1 | 2.72 |
| 0061-03 | 1.03 | 25.0 | MN(III)TPPOAc (.02 g) IM (.02 g) | F | 1.12 | 94.89 | 0.51 | <0.1 | 2.85 |
| 0061-04 | 1.58 | 25.0 | MN(III)TPPOAc (.02 g) IM (.02 g) | F | 1.28 | 94.91 | 0.53 | <0.1 | 2.84 |
| 0061-05 | 2.00 | 25.0 | MN(III)TPPOAc (.02 g) IM (.02 g) | F | 1.09 | 95.02 | 0.56 | <0.1 | 2.88 |
| 0061-06 | 2.60 | 25.0 | MN(III)TPPOAc (.02 g) IM (.02 g) | F | 0.91 | 95.15 | 0.58 | <0.1 | 2.91 |
| 0061-07 | 4.67 | 25.0 | MN(III)TPPOAc (.02 g) IM (.02 g) | F | 0.62 | 95.42 | 0.59 | <0.1 | 2.90 |
| 6225-62 | .08 | 25.0 | MN(III)TPPOAc (.04 g) IM (.04 g) | F | 2.61 | 94.09 | 0.50 | <0.1 | 2.36 |
| 0062-02 | .50 | 25.0 | MN(III)TPPOAc (.04 g) IM (.04 g) | F | 0.27 | 95.91 | 0.70 | <0.1 | 2.60 |
| 0062-03 | 1.00 | 25.0 | MN(III)TPPOAc (.04 g) IM (.04 g) | F | 0.06 | 96.07 | 0.74 | <0.1 | 2.61 |
| 6225-63 | .10 | 10.0 | MN(III)TPPOAc (.04 g) IM (.04 g) | F | 15.49 | 83.07 | 0.08 | <0.1 | 0.91 |
| 0063-02 | .50 | 10.0 | MN(III)TPPOAc (.04 g) IM (.04 g) | F | 14.94 | 83.11 | 0.10 | <0.1 | 1.45 |
| 0063-03 | .92 | 10.0 | MN(III)TPPOAc (.04 g) IM (.04 g) | F | 12.24 | 85.24 | 0.13 | <0.1 | 2.13 |
| 0063-04[c] | 16.0 | 25.0 | MN(III)TPPOAc (.04 g) IM (.04 g) | F | 0.02 | 94.36 | 0.43 | <0.1 | 4.37 |
| 6225-65 | .15 | 33.0 | MN(III)TPPOAc (.04 g) IM (.04 g) | F | 4.34 | 92.37 | 0.35 | <0.1 | 2.60 |
| 0065-02 | .55 | 29.0 | MN(III)TPPOAc (.04 g) IM (.04 g) | F | 1.07 | 94.98 | 0.50 | <0.1 | 3.03 |
| 0065-03 | 1.06 | 27.0 | MN(III)TPPOAc (.04 g) IM (.04 g) | F | 0.36 | 95.46 | 0.57 | <0.1 | 3.15 |
| 0065-04 | 2.00 | 28.0 | MN(III)TPPOAc (.04 g) IM (.04 g) | F | 0.12 | 95.73 | 0.59 | <0.1 | 3.11 |
| 6225-69 | .12 | 37.0 | MN(III)TPPOAc (.04 g) IM (.08 g) | F | 1.32 | 95.02 | 0.46 | <0.1 | 2.78 |
| 0069-02 | .50 | 26.0 | MN(III)TPPOAc (.04 g) IM (.08 g) | F | 0.13 | 95.94 | 0.61 | <0.1 | 2.88 |
| 6225-83 | .20 | 25.4 | MN(III)TPPOAc (.04 g)IM(.04 g)DT(.17 g) | F | 14.48 | 84.04 | 0.089 | <0.1 | 0.96 |
| 0083-02 | .67 | 24.3 | MN(III)TPPOAc (.04 g)IM(.04 g)DT(.17 g) | F | 12.32 | 85.78 | 0.12 | <0.1 | 1.36 |
| 0083-03 | 1.60 | 25.0 | MN(III)TPPOAc (.04 g)IM(.04 g)DT(.17 g) | F | 11.15 | 86.72 | 0.15 | <0.1 | 1.57 |
| 0083-04 | 3.50 | 24.5 | MN(III)TPPOAc (.04 g)IM(.04 g)DT(.17 g) | F | 10.58 | 87.28 | 0.17 | <0.1 | 1.70 |
| 0083-05 | 21.5 | 25.0 | MN(III)TPPOAc (.04 g)IM(.04 g)DT(.17 g) | F | 9.34 | 88.22 | 0.21 | <0.1 | 1.93 |
| 6225-85 | .13 | 30.5 | MN(III)TPPOAc (.04 g)IM(.08 g)DT(.08 g) | F | 5.15 | 91.95 | 0.26 | <0.1 | 2.32 |
| 0085-02 | .58 | 25.0 | MN(III)TPPOAc (.04 g)IM(.08 g)DT(.08 g) | F | 1.22 | 95.07 | 0.43 | <0.1 | 2.89 |
| 0085-03 | 1.06 | 25.0 | MN(III)TPPOAc (.04 g)IM(.08 g)DT(.08 g) | F | 0.60 | 95.56 | 0.40 | <0.1 | 3.04 |
| 0085-04 | 3.33 | 25.0 | MN(III)TPPOAc (.04 g)IM(.08 g)DT(.08 g) | F | 0.13 | 95.80 | 0.54 | 0.03 | 3.02 |
| 6225-88 | .17 | 35.5 | MN(III)TPPOAc (.04 g)IM(.08 g)DT(.17 g) | F | 4.75 | 92.40 | 0.31 | 0.06 | 1.97 |
| 0088-02 | .62 | 27.0 | MN(III)TPPOAc (.04 g)IM(.08 g)DT(.17 g) | F | 2.20 | 94.53 | 0.42 | 0.05 | 2.39 |
| 0088-03 | 2.00 | 25.8 | MN(III)TPPOAc (.04 g)IM(.08 g)DT(.08 g) | F | 1.16 | 95.40 | 0.42 | 0.05 | 2.55 |
| 6225-93 | .18 | 36.6 | MN(III)TPPOAc (.04 g)IM(.12 g) | F | 0.77 | 95.71 | 0.62 | <0.1 | 2.49 |
| 0093-02 | .62 | 28.0 | MN(III)TPPOAc (.04 g)IM(.12 g) | F | 0.10 | 96.35 | 0.61 | <0.1 | 2.54 |

TABLE II-continued

Decomposition of TBHP in the Presence of Various Catalysts

| Notebook Number | Time (Hrs) | Temp (°C.) | Catalysts[a] | Reactor[b] | TBHP | TBA | Acetone | Methanol | DTBP |
|---|---|---|---|---|---|---|---|---|---|
| — | | | Starting Material | | 20.20 | 79.28 | 0.007 | 0 | 0.06 |

[a]TPP = meso-tetraphenylporphine; OAC = acetate; IM = imidazole; AcAc = acetylacetonate; DT = dodecane thiol
[b]T = 150 ml Fisher-Porter tube, 15.0 g scale
F = 200 ml round-bottomed flask, 20.0 g scale
[c]Allowed to warm to 25° C. overnight Table II shows some experiments with imidazole and manganese (III) tetraphenyl porphine acetate. Note here also that the acetone remains below 1%. Exp. No. 0061-07 shows after 4.67 hours at 25° C., 0.62 wt. % TBHP remaining and only 0.59% of the low value by-product acetone. Higher concentrations of catalyst produce even lower concentrations of TBHP and the percent acetone remains significantly below 1%. See 0062-03, 0063-04, 0065-04 and 0069-02.

Having thus described our invention, what is claimed is:

1. In a method wherein a t-butyl hydroperoxide charge stock is brought into contact with a catalytically effective amount of a decomposition catalyst in a hydroperoxide decomposition zone under hydroperoxide decomposition conditions in liquid phase with agitation to convert said t-butyl hydroperoxide to decomposition products, principally t-butyl alcohol, the improvement which comprises:
   (a) using a metal porphine compound as said decomposition catalyst, and optionally conducting the hydroperoxide decomposition in the additional presence of a $C_1$-$C_{18}$ alkyl thiol or a heterocyclic amine selected from the group consisting of pyridine, quinoline, isoquinoline, imidazole, 1-alkyl imidazoles and 2-alkyl imidazoles, wherein the alkyl group contains 1 to 4 carbon atoms, or a mixture thereof and
   (b) recovering said t-butyl alcohol from the products of said reaction,
   (c) said metal of said metal porphine compound being selected from the group consisting of iron, manganese, nickel, palladium, ruthenium, vanadium and zinc.

2. A method as in claim 1 wherein the decomposition reaction is conducted in the additional presence of an effective amount of a $C_1$-$C_{18}$-alkyl thiol.

3. A method as in claim 2 wherein the alkyl thiol is dodecane thiol.

4. A method as in claim 1 wherein the decomposition reaction is conducted in the additional presence of an effective amount of a heterocyclic amine selected from the group consisting of pyridine, quinoline, isoquinoline, imidazole, 1-alkyl imidazoles and 2-alkyl imidazoles, wherein the alkyl group contains 1 to 4 carbon atoms.

5. A method as in claim 4 wherein the heterocyclic amine is pyridine.

6. A method as in claim 4 wherein the heterocyclic amine is quinoline.

7. A method as in claim 4 wherein the heterocyclic amine is isoquinoline.

8. A method as in claim 4 wherein the heterocyclic amine is imidazole or a 1-alkyl or 2-alkyl imidazole wherein the alkyl group contains from 1 to 4 carbon atoms.

9. A method as in claim 8 wherein the heterocyclic amine is imidazole.

10. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, wherein unreacted isobutane is continuously separated from said initial reaction mixture to provide a charge stock comprising a solution of said t-butyl hydroperoxide in said t-butyl alcohol, wherein said charge stock is continuously charged to a hydroperoxide decomposition zone, and wherein a catalytic hydroperoxide decomposition reaction is continuously conducted in said decomposition reaction zone to convert said t-butyl hydroperoxide to decomposition products, principally t-butyl alcohol, to provide a hydroperoxide conversion product, the improvement which comprises:
   (a) conducting said hydroperoxide decomposition reaction in the presence of about 0.001 to about 5 wt. %, based on the weight of said charge stock of an iro (III) or manganese (III) porphine catalyst and in the additional presence of from about 0.2 to about 5 parts by weight, per part of said porphine catalyst of a $C_1$-$C_{18}$ alkyl thiol and in the further presence of from about 0.2 to about 5 parts by weight, per part of said porphine catalyst of a heterocyclic amine by contacting said t-butyl hydroperoxide in said hydroperoxide decomposition zone in liquid phase with agitation with said decomposition catalyst in solution in said t-butyl alcohol, under reaction conditions including a temperature within the range of about 20° to about 125° C. and autogenous pressure,
   (b) continuously removing a stream of said hydroperoxide conversion product from said hydroperoxide conversion reaction zone,
   (c) continuously separating said stream of said hydroperoxide conversion product stream into an isobutane fraction and a t-butyl alcohol fraction, and
   (d) continuously recovering t-butyl alcohol from said t-butyl alcohol fraction.
   (e) said heterocyclic amine being selected from the group consisting of pyridine, quinoline, isoquinoline, imidazole, 1-alkyl imidazoles and 2-alkyl imidazoles, wherein the alkyl group contains 1 to 4 carbon atoms.

11. A method as in claim 10 wherein the alkyl thiol is dodecane thiol.

12. A method as in claim 10 wherein the heterocyclic amine is pyridine.

13. A method as in claim 10 wherein the heterocyclic amine is quinoline.

14. A method as in claim 10 wherein the heterocyclic amine is isoquinoline.

15. A method as in claim 10 wherein the heterocyclic amine is imidazole or a 1-alkyl or 2-alkyl imidazole wherein the alkyl group contains from 1 to 4 carbon atoms.

16. A method as in claim 15 wherein the heterocyclic amine is imidazole.

17. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, wherein unreacted isobutane is continuously separated from said initial reaction mixture to provide a charge stock comprising a solution of said t-butyl hydroperoxide in said t-butyl alcohol, wherein said charge stock is continuously charged to a hydroperoxide decomposition zone, and wherein a catalytic hydroperoxide decomposition reaction is continuously conducted in said decomposition reaction zone to convert said t-butyl hydroperoxide to decomposition products, principally t-butyl alcohol, to provide a hydroperoxide conversion product, the improvement which comprise:

(a) conducting said hydroperoxide decomposition reaction in the presence of about 0.001 to about 5 wt. %, based on the weight of said charge stock of an iron or manganese meso-tetraphenylporphine carboxylate or halide, in the additional presence of from about 0.2 to about 5 parts by weight, per part of said porphine catalyst of a $C_1$–$C_{18}$ alkyl thiol and in the further presence of from about 0.2 to about 5 parts by weight, per part of said porphine catalyst of an imidazole selected from the group consisting of imidazole, $C_1$–$C_4$ 1-alkyl imidazoles and $C_1$–$C_4$ 2-alkyl imidazoles by contacting said t-butyl hydroperoxide in said hydroperoxide in said hydroperoxide decomposition zone in liquid phase with agitation with said decomposition catalyst in solution in said t-butyl alcohol, under reaction conditions including a temperature within the range of about 20° to about 125° C. and autogenous pressure, (b) continuously removing a stream of said hydroperoxide conversion product from said hydroperoxide conversion reaction zone, (c) continuously separating said stream of said hydroperoxide conversion product stream into an isobutane fraction and a t-butyl alcohol fraction, and (d) continuously recovering t-butyl alcohol from said t-butyl alcohol fraction.

* * * * *